United States Patent [19]
Easton et al.

[11] Patent Number: 5,378,232
[45] Date of Patent: Jan. 3, 1995

[54] INJECTION/ACTIVATION APPARATUS

[75] Inventors: Thomas G. Easton, Coram; Edward Reich, Setauket, both of N.Y.

[73] Assignee: Orion Therapeutic Systems, Inc., New York, N.Y.

[21] Appl. No.: 750,920

[22] Filed: Aug. 28, 1991

[51] Int. Cl.$^6$ .................................................. A61M 37/00
[52] U.S. Cl. ......................................... 604/82; 604/85
[58] Field of Search ................. 604/20, 49, 82–85, 604/891.1; 128/829.1, 898

[56] References Cited

U.S. PATENT DOCUMENTS

| | | | |
|---|---|---|---|
| 3,950,513 | 4/1976 | Jensen | 424/94 |
| 4,484,909 | 11/1984 | Urquhart et al. | 604/82 |
| 4,540,403 | 9/1985 | Theeuwes | 604/85 |
| 4,681,582 | 7/1987 | Yamamoto | 604/84 |
| 4,695,272 | 9/1987 | Berglund et al. | 604/85 |
| 4,705,503 | 11/1987 | Dorman et al. | 604/50 |
| 4,715,850 | 12/1987 | Tran | 604/82 |
| 4,715,851 | 12/1987 | Geisser et al. | 604/82 |
| 4,722,726 | 2/1988 | Sanderson et al. | 604/20 |
| 4,740,103 | 4/1988 | Theeuwes | 604/83 |
| 4,774,087 | 9/1988 | Wu et al. | 424/94.64 |
| 4,790,820 | 12/1988 | Theeuwes | 604/85 |
| 4,842,577 | 6/1989 | Konno et al. | 604/20 |
| 4,871,352 | 10/1989 | Tran | 604/82 |
| 4,915,689 | 4/1990 | Theeuwes | 604/82 |
| 4,978,336 | 12/1990 | Capozzi et al. | 604/82 |
| 4,978,337 | 12/1990 | Theeuwes | 604/85 |

FOREIGN PATENT DOCUMENTS 0182579 5/1986 European Pat. Off. .
2497229 7/1982 France .

OTHER PUBLICATIONS

K. Reddy and C. Wagner, Studies on the Stability of Plasmin, Chemical Abstracts, vol. 98, 1983, p. 330.
K. Takagi and Y. Yabushita, Antithrombotic Preparations for Medical Use, Chemical Abstracts, vol. 104, 1986, p. 393.
Ambrus et al., *The Pharmacologist*, 1:57 (1959).
Amris et al., *Danish Medical Bulletin*, 11:146–152 (1964).
Amris et al. *Scand. J. Clin. & Lab. Investigation*, 15:179–188 (1963).
Amris et al., *Scand. J. Clin. & Lab. Investigation*, 18:1–33 (1966).
Back et al., *Circulation Research*, IV:440–443 (1956).
Back et al., *J. Clin. Invest.*, 37:864–871 (1958).
Bell et al., *Nature*, 282:525–527 (1979).
Cliffton, *J. Am Geriatrics Soc.*, 6:118–127 (1958).
Cliffton, *Annal. N.Y. Acad. Sci.*, 68:209–229 (1957).
Cook et al., *Trends in Pharmaceutical Sciences;* 11:444–451 (1990).
Dano et al., *Biochim. Biophys. Acta*, 566:138–151 (1979).
Duckert et al., in *New Concepts in Streptokinase Dosimetry*, Martin, Schoop & Hirsh, eds., Hans Huber Publishers, Bern–Stuttgart, 1978, pp. 175–178.
Edy et al., *Thrombosis Research*, 8:513–518 (1976).
Evans, C. H. in *Biochemistry of the Lanthanides*, Plenum Press, New York, pp. 85–125, 1990.
Hedner et al, *Blood*, 51:157–164 (1978).
Hirsh, in: *New Concepts in Streptokinase Dosimetry*, Martin, Schoop & Hirsh, eds., Hans Huber Publishers, Bern-Stuttgart, 1978, pp. 239–243.
Latallo et al., *Aktulle Probleme in der Angiologie*, 26:181–190 (1975).
Liu et al., *Canadian J. Biochem.*, 49:1055–1061 (1971).
Marbet et al., *Thromb. Haemostas.*, 48:187–200 (1982).
Matsuo et al., *Nature*, 291:590–591 (1981).
Mizutani et al., *Japanese Circulation J.*, 51:822 (1987).
Powell et al., *J. Biol. Chem.*, 255:5329–5335 (1980).
Shi et al., *J. Biol Chem.*, 263:17071–17075 (1988).
Sottrop-Jensen et al., in *Progress in Chemical Fibrinolysis and Thrombolysis*, vol. 3, Davidson et al., eds., Raven Press, N.Y., 1978, pp. 191–209.

*Primary Examiner*—C. Fred Rosenbaum
*Assistant Examiner*—Michael Rafa
*Attorney, Agent, or Firm*—Weingarten, Schurgin, Gagnebin & Hayes

[57] ABSTRACT

Disclosed is apparatus for administration of a drug in active form, which includes means defining a prodrug reaction zone including an immobilized enzyme for modifying chemically a prodrug to a physiologically compatible, physiologically active drug form, means in communication with the reaction zone for establishing parenteral access to the body of a patient, and means for transporting a prodrug through the reaction zone at a rate sufficient to convert the prodrug to the active drug form and then into the body of a patient.

26 Claims, 4 Drawing Sheets

INJECTION/ACTIVATION APPARATUS

The invention relates to an apparatus useful for the parenteral administration of a therapeutic agent to a human patient.

BACKGROUND OF THE INVENTION

The parenteral administration of a therapeutic agent is used extensively as an integral part of the daily treatment of medical and surgical patients. Liquids commonly administered parenterally include blood, blood substitutes, plasma substitutes, and solutions of dextrose, sodium chloride, or other electrolytes.

U.S. Pat. No. 4,790,820 discloses a parenteral delivery system for administering an agent, which includes a drip chamber and a formulation chamber. The formulation chamber may include an ion exchange resin to which the drug to be administered is releasably bonded.

U.S. Pat. No. 4,540,403 discloses a parenteral delivery system for administering an agent to a recipient, which includes an electrotransport apparatus that admits the agent at an electrically controlled rate into fluid that flows through the parenteral system over delivery time.

SUMMARY OF THE INVENTION

The invention in its broadest aspects implements the concept of modifying a prodrug, by chemical reactions, to convert the prodrug to an active, physiologically compatible form immediately prior to, e.g., during the process of, its parenteral administration to a patient, the prodrug typically occurring in some storage stable, soluble, toxic, and/or inactive form. Parenteral administration may include infusion via intravenous, intraarterial, intraperitoneal, or subcutaneous routes. As used herein, "prodrug" refers to any form of a drug or drug precursor, either active or inactive, which can be chemically modified to a pharmacologically or physiologically desirable form. The conversion of prodrug is accomplished by providing at the site of drug treatment, e.g., in line between a reservoir of the prodrug and a trocar or other entry point into the patient's body, a reactor having a reaction zone comprising biological macromolecules, such as an enzyme preparation, or another device which chemically modifies the prodrug, e.g., an ion exchange medium or ion adsorbing means, both for extracting ions. The modifying agent is by nature, construction, or composition designed to be retained selectively at or near the site of reaction, and thus prevented from accompanying the active drug into the patient's body.

The apparatus of the invention can be embodied in many forms, and adapted to many specific drug treatment protocols. The invention can be used, for example, in an implantable drug pump so as to permit storage in stabilized form or at high concentration in solution in a reservoir disposed within or adjacent to the pump housing. Passage of the stored prodrug through the reaction zone can, for example, enzymatically modify the soluble form to active, but less soluble form; or modify the stable but inactive, or low activity, or toxic prodrug to active, physiologically compatible form just prior to the time the drug is introduced into the body; or modify an active drug from a form that is preferred for storage to another active form that is physiologically or pharmacologically more desirable. Alternatively, the reaction zone can be disposed between a reservoir of prodrug and the skin in a transdermal patch.

Thus, in-one aspect, the invention features an apparatus for administration of a drug in active form, the apparatus including means defining a prodrug reaction zone comprising an immobilized biological macromolecule, e.g., an enzyme, for modifying chemically a prodrug to a physiologically compatible, physiologically active drug form, means in communication with the reaction zone for establishing parenteral access to the body of a patient, and means for transporting a prodrug through the reaction zone at a rate sufficient to convert inactive prodrug to active drug and then into the body of a patient.

In preferred embodiments, the reaction zone includes a high surface area matrix having immobilized thereon the macromolecule, e.g, an enzyme immobilized on the matrix. The matrix may be an insoluble or soluble substance capable of binding an enzyme; if insoluble, it may be a porous membrane, e.g., nylon, or may comprise insoluble chromatographic particles such as those used in column chromatography, e.g., microbeads; if soluble, it may include soluble macromolecules capable of being selectively retained, e.g., by a filter, within the reaction zone.

In one preferred species of the invention, a plasminogen activator, e.g., urokinase or tissue plasminogen activator immobilized in the reaction zone cleaves the prodrug plasminogen, or an analog thereof having the properties of plasminogen, to produce the active drug plasmin or an enzymatically active analog thereof. Analogs of plasminogen include not only recombinant or synthetic versions of the complete molecule that, when converted to plasmin, retain the activities of native plasmin, but also truncated versions of plasminogen, e.g., mini-, micro-, or lys-plasminogen. Alternatively, the enzyme may be a protease, e.g., plasmin, and the prodrug a prohormone, e.g., proinsulin, which is converted by the protease plasmin into the active hormone insulin.

In another aspect, the invention features an apparatus for fibrinolysis/fibrinogenolysis therapy capable of delivering plasmin to the site of an intravascular thrombus in a patient at a rate and concentration independent of the patient's vascular plasminogen concentration. The apparatus includes a reservoir of plasmin stabilized by the presence of an additive, e.g., lauryl sulfate ions, ion removing means for removing lauryl sulfate ions from the stabilized plasmin thereby to convert the stabilized plasmin to physiologically compatible, fibrinolytically/fibrinogenolytically active form, and means defining a flow path for establishing flow of stabilized plasmin from the reservoir through the ion removing means, and a flow of fibrinolytically/fibrinogenolytically active plasmin from the ion removing means parenterally into the body of the patient.

In preferred embodiments, the reservoir includes a reservoir of lauryl sulfate-stabilized plasmin; and the ion removing means may include an ion exchange resin or an ion adsorbing substance, e.g., a hydrophobic matrix. Preferably other hydrophobic anions or cations may also be used in place of lauryl sulfate.

In yet another aspect, the invention features another apparatus for fibrinolysis/fibrinogenolysis therapy capable of delivering a fibrinolytically/fibrinogenolytically active protein to the site of an intravascular thrombus in a patient at a rate and concentration independent of the patient's vascular plasminogen concentration.

The apparatus includes a reservoir of a protein-prodrug selected from the group consisting of plasminogen, a serine protease-activatable analog of plasminogen, and a mixture thereof, a protein-prodrug reaction zone including an immobilized biological macromolecule operative to convert the protein-prodrug to a fibrinolytically/fibrinogenolytically active protein, and means defining a flowpath for establishing a flow of protein-prodrug from the reservoir to the protein-prodrug reaction zone, and a flow of fibrinolytically/fibrinogenolytically active protein from the reaction zone parenterally into the body of the patient.

In preferred embodiments, the reaction zone includes a matrix having a plasminogen activator bound thereto; preferably, the means defining the flowpath includes a conduit communicating between the reaction zone and a trocar for accessing the body of the patient. Preferably, the protein-prodrug is selected from the group consisting of mini-plasminogen, micro-plasminogen, glu-plasminogen, and lys-plasminogen.

In yet another aspect of the invention, the invention features an apparatus for delivering to a site of action an autolytic protease in an active form. The apparatus includes a reservoir of an autolytic enzyme preparation stabilized by the presence of lauryl sulfate, ion removing means for removing lauryl sulfate ions from the preparation thereby to convert the stabilized preparation to physiologically compatible, enzymatically active form, and means defining a flow path for establishing a flow of stabilized preparation from the reservoir and through the ion-removing means, and a flow of physiologically compatible, active enzyme from the ion-removing means to the site of action.

In preferred embodiments, the site of action is the human body and the apparatus further includes means for parenteral delivery of the active enzyme into the body; and the ion removing means may be an ion adsorbing or an ion exchange resin. An adsorbing means is capable of removing ionic or amphipathic detergents that inhibit the autolysis of plasmin.

The injection/activation apparatus of the invention is compact, small, and economical. Because the prodrug is chemically modified to an active drug as it passes through the reaction zone, substantially coincident with injection of the drug into the body of the patient, there is little elapsed time between modification of the drug and its administration to the patient. Consequently, there is little opportunity for loss of the enzymatic activity of the active drug prior to its administration to the patient. In addition, if an enzyme immobilizer is used that possesses a large surface area, the immobilizer will be capable of binding large amounts of enzyme, and useful for repeated dosages of drug. Since the conversion rate of prodrug to drug by immobilized enzyme using the apparatus of the invention is quantifiable using the apparatus of the invention, an accurately quantified amount of active drug may be administered to the patient, thus providing a precise calculation of the level of administered drug and dependable, e.g., thrombolytic, effects.

DESCRIPTION

Figure 1:
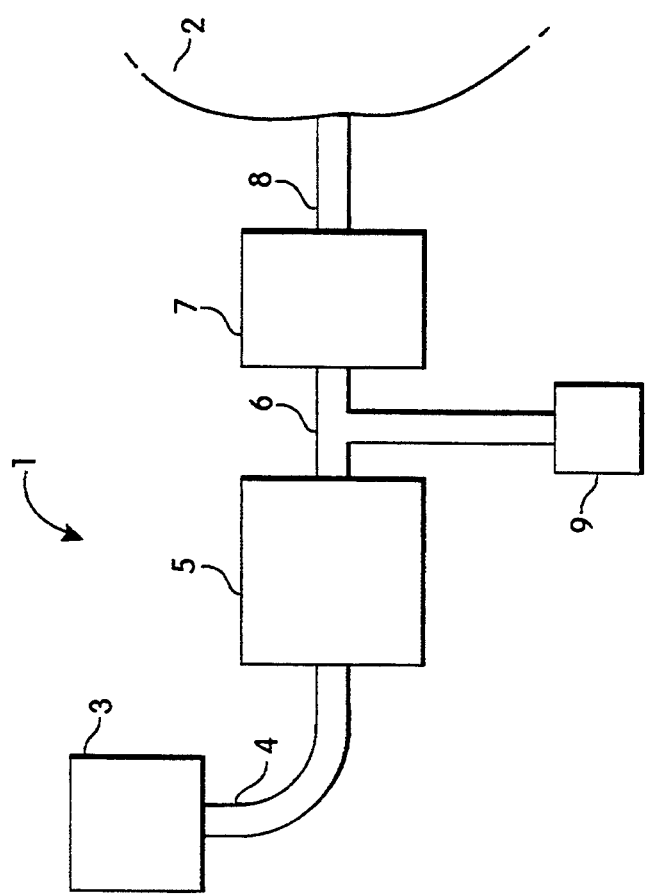
FIG. 1 schematically illustrates the apparatus of the invention.

The apparatus 1 of the invention, for converting prodrug to drug upon delivery of drug to the body, is schematically shown in FIG. 1. Reservoir 5 contains a prodrug which is delivered via delivery port 6 to reaction zone 7. The prodrug is converted to active drug by a biological macromolecule within reaction zone 7. The active drug is then delivered via delivery port 8 to the patient 2. In addition, container 3 may hold a physiologically compatible solution for dissolving or diluting prodrug in reservoir 5 which is delivered to reservoir 5 via delivery port 4. Alternatively, or in addition, pump 9, e.g., a peristaltic pump, may propel prodrug from reservoir 5 through port 6 to reaction zone 7.

Figure 2B:
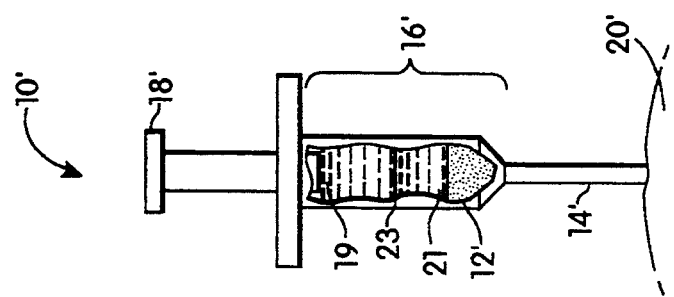
FIGS. 2A and 2B illustrate two similar embodiments of an injection/activation apparatus according to the invention.
Figure 2A:
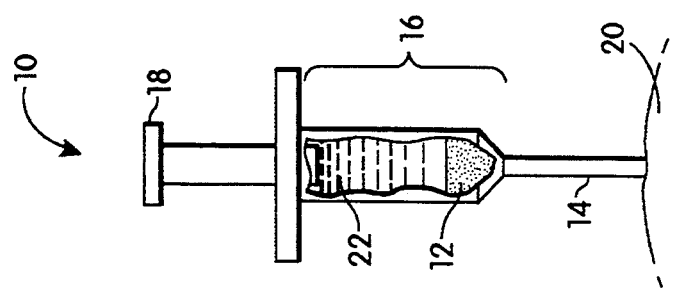

Other embodiments 10 and 10' of the injection/activation apparatus of the invention are shown in FIGS. 2A and 2B. The apparatus of FIG. 2A includes a reservoir 22 for holding a prodrug, a prodrug reaction zone 12 which includes an immobilized biological macromolecule such as an enzyme for chemically modifying a prodrug to a physiologically compatible, physiologically active drug form; a conduit 14 in communication with the reaction zone 12 and capable of establishing parenteral access to the body of a patient, e.g., through a trocar (not shown); and a plunger 18 and housing 16 for transporting a prodrug through the reaction zone at a rate sufficient to convert the prodrug to the active drug form.

In the embodiment of the invention shown in FIG. 2A, conduit 14 can include a trocar, e.g., a beveled needle capable of piercing the patient's skin and inserting into a blood vessel. Prodrug reaction zone 12 is contained within housing 16 which includes reservoir 22 for containing the prodrug. The prodrug is transported by the action of plunger 18 through reaction zone 12 within housing 16, into contact with the immobilized enzyme immobilized thereon, and then through conduit 14 and into the body 20 of the patient.

The apparatus of the invention may be used to inject a drug in its active form into the human body, wherein conversion of the drug from its inactive to active form occurs substantially coincident with the introduction of the drug into the patient's body, i.e., either during the process or immediately prior thereto. The time period between the conversion of prodrug to drug and injection of the drug into the body will typically be a period less than 10 minutes, preferably less than 5 minutes, and most preferably less than 1 minute. "Immediately prior to" means that the prodrug to drug conversion and the introduction of drug into the patient occur close enough in time such that the active drug maintains at least 80%, preferably 90–99%, activity during that intervening time period. Preferably, plasmin made according to the invention is substantially free of elements that interfere with its clot-lysing ability; it may be 98–99% pure plasmin, except for the presence of plasminogen in the plasmin sample. Thus, in operation, pressure applied to plunger 18 pushes prodrug from reservoir 22 through reaction zone 12 and conduit 14 and into the body 20 of the patient. As the prodrug is pushed through prodrug reaction zone 12, it is converted by the immobilized enzyme into active drug. Thus, during the process of injection, the drug is converted from an inactive, i.e., a prodrug form, to an active, i.e., a drug form, by exposure to immobilized enzyme. The immobilized enzyme, contained within the injection apparatus is retained selectively within the reaction zone 12 and normally does not accompany the active drug through conduit means 14 to the body; i.e., it is only the active drug that is administered to the patient.

In a similar embodiment, shown in FIG. 2B, wherein corresponding parts are identified by primed numbers, prodrug is contained within reservoir 21 and solvent is contained within reservoir 19; reservoirs 19 and 21 are separated by barrier 23, which may be, e.g., a pressure frangible partition. In operation, pressure applied to plunger 18' shatters barrier 23 by pushing solvent from reservoir 19 into prodrug reservoir 21; solvent and prodrug are thus reconstituted before encountering reaction zone 12'.

Figure 3A:
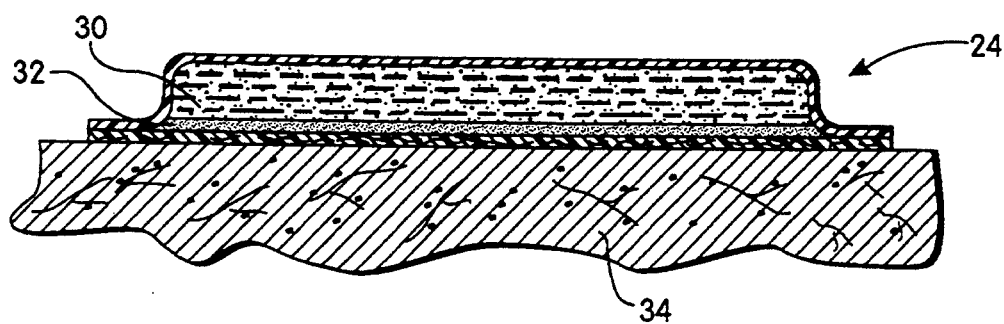
FIGS. 3A and 3B illustrate two different views of a transdermal patch.
Figure 3B:
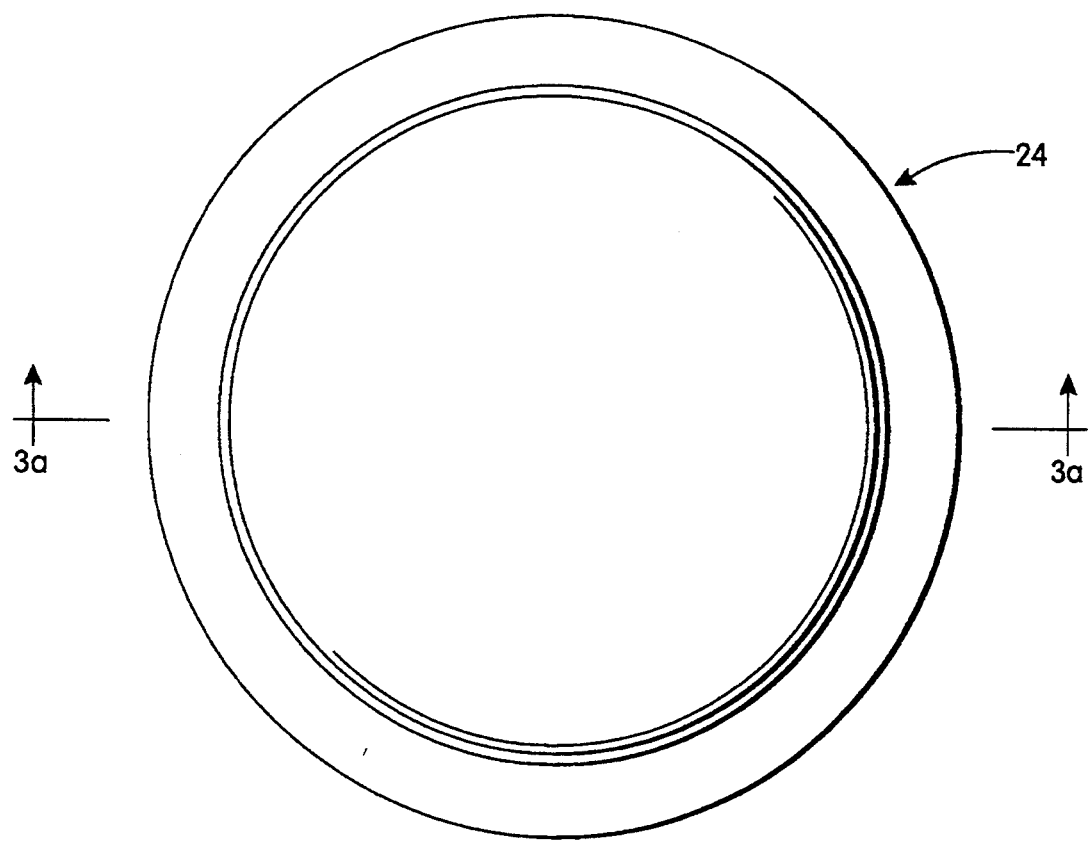

Another embodiment of the invention is shown in FIGS. 3A and 3B, which schematically illustrate in cross-section (3A) and plan view (3B) a transdermal patch 24 in which reservoir 30 contains inactive prodrug. The prodrug moves, e.g., by diffusion, from reservoir 30 through a reaction zone 32 and into the patient's skin 34. Coincident with movement of the prodrug through reaction zone 32, inactive prodrug is converted to active drug by a macromolecule that is contained within reaction zone 32.

Immobilized macromolecules useful in the invention include any biochemical entity capable of promoting reactions including, but not limited to, electrochemical attractions, chemical reductions, oxidations, deacylations, phosphorylations, hydrolytic reactions, and condensations, or other enzymatic or catalytic reactions. Such macromolecules may include proteins and related cofactors such as coenzymes, polysaccharides, nucleic acids, or lipids.

The immobilized enzyme may be coupled either reversibly or irreversibly to a matrix that may include soluble polymers or molecules separable by size or by specific ligands (e.g., an affinity ligand or an immunoglobulin having specificity for the enzyme) from the drug destined for injection. A soluble matrix may be retained in the apparatus upon injection of the drug by a filter calibrated to retain the matrix-bound enzyme, but permit passage of the drug. Alternatively, the enzyme be attached to an insoluble matrix, e.g., made of a synthetic or natural material. An insoluble matrix may include a variety of forms, e.g., membranes, porous filters, chromatographic support, or magnetic particles, all of which readily and selectively are retained by mechanical or magnetic means, but are so disposed as to ensure contact with the prodrug.

The enzyme may be immobilized to a matrix which may be derivatized to bind the enzyme according to conventional chemical procedures well-known to those skilled in the art. Suitable membranes include those consisting of nylon, preferably those having a high density of derivatized chemical residues, such as free amino or carboxylate groups. Other examples include porous membranes consisting wholly or largely of cellulose-derived matrices, also preferably carrying a high density of carboxylate groups. Supporting matrices of this type have extensive surface area and may be arranged singly, in stacks, or in alternative forms such as sheets or discs of desired thickness. These properties enable the immobilization of a high density of enzyme and, thus, the achievement of a high prodrug conversion rate in a compact volume and at a minimal cost. A porous membrane may be prepared for enzyme immobilization as follows.

Preparation of Immobilization Membrane

Membrane sheets (Pall Corp., Glen Cove, N.Y., Biodyne C membrane No. BNPCH5 or BNNCH5) are first cut into the shape of discs of desired diameter, then derivatized as follows. A solution of 0.5M spermine tetrahydrocholoride in water is brought to pH 7.0–7.1 by the careful addition of NaOH; separately, a solution of a water soluble carbodiimide, preferably 1-ethyl-3-(3 dimethylaminopropyl) carbodiimide hydrochloride (EDAC), (also 0.5M in water) is brought to pH 5.0–5.05 by the addition of dilute hydrochloric acid; the two solutions are mixed in equal amounts and membrane discs are immersed in the mixture and incubated overnight at room temperature. The discs are washed copiously first with distilled water and then with 1.0M $NaHCO_3$. The discs are then packed in solid, finely-pulverized succinic anhydride (500 mg per $cm^2$ disc surface area), and sufficient dipotassium hydrogen phosphate (e.g., 0.5M) is added to thoroughly irrigate the disc and succinic anhydride packing (e.g., 0.3–0.5 ml/$cm^2$ disc area). The reaction is allowed to proceed overnight at room temperature. Small sample discs are incorporated alongside the membranes being treated and are tested for the presence of residual free amino groups. This succinylation procedure can be repeated, if necessary. The succinylated discs are rinsed free of precipitated succinate, washed under suction first with $NaHCO_3$ (0.5–1.0M) and then with water, and dried. The discs may be stored for months at room temperature, with no change in properties.

The dried membrane filter discs are mounted and securely clamped in holders that permit them to be perfused, and the entire assembly is incorporated into a circuit, driven by a peristaltic pump, in which the discs are continuously perfused for at least 1 hour at approximately 30°–37° C. with a solution of N-hydroxysuccinimide and EDAC, both at 50 mM, in pure tert-butanol. At the end of the perfusion, the mounted discs are perfused briefly with 1 mM HCl at room temperature, blotted, swirled in ice-cold distilled water for a few minutes, then placed in a shallow dish, previously rinsed with 0.5% detergent (Triton X-100) in water, whose diameter is just sufficient to accommodate the membrane discs. At this stage, the discs are capable of immobilizing an enzyme. Examples of immobilized enzymes include, but are not limited to, those described herein, i.e., immobilized urokinase and immobilized plasmin.

Fibrinolysis/Fibrinogenolysis Treatment

The injection/activation apparatus of the invention may be used for fibrinolysis/fibrinogenolysis, i.e., treatment of a blood vessel occlusion, such as occurs in medical conditions such as myocardial infarction, thrombophlebitis or other forms of venous thrombosis, or pulmonary embolism. A fibrin/fibrinogen dissolving enzyme, e.g., human plasmin, may be administered directly using the apparatus of the invention to a patient suffering from vessel obstruction by a blood clot or to a patient in danger of developing a clot. Prodrug is contained within housing 5 of the apparatus (FIG. 1); prodrug reaction zone 7 contains an immobilized plasminogen activator. The enzymatically inactive prodrug, plasminogen, is converted coincident with its administration to the enzymatically active drug, plasmin. Active plasmin then travels through the circulatory system and dissolves a blood clot by converting the insoluble structural fibrin matrix of the clot to soluble fragments or, where a clot has not yet developed, lowers the circulating levels of fibrinogen and thus avoids clot formation. The use of the injection/activation apparatus of the invention for fibrinolysis/fibrinogenolysis is described below.

Preparation of Immobilized Plasminogen Activators

The injection/apparatus of the invention may contain a plasminogen activator immobilized on a matrix. Plasminogen activators useful in this embodiment of the invention include, but are not limited to urokinase (UK) and tissue plasminogen activator (tPA). Streptokinase (SK) may also be used as a plasminogen activator according to the invention, but would be most useful if modified, e.g., using recombinant DNA techniques, so as to be insensitive to plasmin degradation.

Immobilized plasminogen activators may be prepared using a highly porous, physically and chemically stable membrane having extensive surface area. The membrane may consist of nylon having 1-3 $\mu$ average pore size, (Pall Corporation, Glen Cove, N.Y.). In its preferred version, such a membrane bears a high density of unsubstituted carboxylate groups (Pall. No. BNPCH5 or BNNCH5) which act as starting points for chemical modifications that allow anchoring of proteins.

Highly purified human urinary urokinase is coupled to membrane discs, such as those described above, immediately after activation. Lyophilized urokinase, e.g., Winkinase (Winthrop Laboratories, Sterling Drug, Inc., N.Y., N.Y.), or Ukidan (Serono, Aubonne, Switzerland) is dissolved in 10 mM HEPES, pH 7.0-7.4 at a concentration of 4-5 mg per ml. Sufficient solution is pipetted into small shallow dishes so as thoroughly to impregnate the activated membranes, e.g., 15-20 $\mu$l/1 cm$^2$ of membrane. A total of approximately 400 $\mu$g or 1.2 mg urokinase is used to impregnate a membrane of 25 mm or 47 mm diameter, respectively. After immersing the membranes in urokinase solution, the dishes are sealed, and incubated in a moist chamber at 4° for 14-16 hours, preferably with gently rocking agitation. The coupled membrane is rinsed with 1 mM HCl by low speed centrifugation in a polypropylene tube, and the rinsing fluid collected, pooled with residual incubation medium, and assayed for remaining non-membrane-bound enzyme. Membrane bound urokinase may be assayed using the urokinase substrate plasminogen, which is converted to fibrinolytically/fibrinogenolytically active plasmin upon exposure to the plasminogen activator urokinase, or a low molecular weight substrate such as N-tosyl-L-arginine methylester.

Preparation of Substrate Plasminogen

Human plasminogen is prepared at 4° C. according to a modified procedure of Liu et al., *Canadian Journal Biochem.* 49:1059-1061 (1971). Five hundred grams of frozen Cohn fraction III or II & III paste is pulverized at 4° C. using a mortar and pestle, then added in portions with constant stirring to 5 liters of phosphate buffered saline (PBS), containing 1 $\mu$M p-nitrophenyl-p-guanidinobenzoate. Stirring is continued for 4-5 hours, until the paste is thoroughly and evenly suspended. The solution is then centrifuged at 12000$\times$g for 20 minutes at 4°, and the gelatinous pellet discarded. The supernatant is filtered under gravity through "fast" filter paper, then brought to 10% of saturation (e.g. 50 g/l), by the addition of solid ammonium sulfate, and centrifuged once again at 12000$\times$g for 20 minutes at 4°. The resulting pellet is discarded, and the lipid-like material floating on the supernatant removed by filtration through a gauze plug.

The filtered supernatant is then pumped, e.g., at 600-900 ml per hour, into e.g., a 230 ml, 4.8$\times$15 cm column packed with G-15 Sephadex in PBS, and the outflow passed directly into a second column, of, e.g., 750-800 ml volume and 10 cm in diameter, packed with lysine-agarose (Pharmacia, 4B or 6B, Piscataway, N.J.) and pre-equilibrated with PBS. The entire system is washed with PBS (e.g., 250 ml), the G-15 column disconnected, and the lysine-agarose column is washed with an additional 1.5 column volumes of PBS until the $A_{280}$ drops below 0.15. The column is then washed with 1 column volume of a solution consisting of 4 parts of ethylene glycol and 6 parts of potassium phosphate buffer (0.5M, pH 8.0), followed by one column volume of PBS. Plasminogen is then eluted from the column with a linear gradient (2.5-3 column volumes) of epsilon aminocaproic acid (0-25 mM) in PBS, and collected in fractions. The fractions having the highest concentration of protein are pooled and precipitated at 50% saturated ammonium sulfate in the presence of benzamidine (50 mM), the pH being kept near neutrality by periodic addition of small volumes of tris-hydroxymethyl aminomethane (tris) base (1M).

The precipitated plasminogen can be stored under 50% saturated ammonium sulfate containing 50 mM benzamidine for many months with no less of activity. After desalting and redissolving in PBS, it can be used directly for generating plasmin, as described below.

Preparation of Substrate Mini-plasminogen

Truncated forms of plasminogen such as mini- or micro-plasminogens, or derivatives thereof, may also be used for the generation of correspondingly truncated forms of plasmin. Mini-plasminogen is prepared according to a modified procedure of Powell et al., *J. Biol. Chem.* 225:5329-5335 (1980). The plasminogen precipitate, e.g., 300 mg, is suspended in ammonium sulfate-benzamidine, as described above, centrifuged at 10,000$\times$g for 30 minutes at 4° C. and the resulting supernatant discarded. The pellet is dissolved in a minimum volume e.g., 15-20 ml, of 100 mM NaCl-50 mM Tris, pH 8.0, at 4° C. and desalted by passage through a 230 ml, 4.8$\times$15 cm column of G15 Sephadex in the cold. Protein-containing fractions eluted from the column are pooled and diluted at room temperature with starting NaCl-Tris buffer to 3 mg/ml. 20,000 kallikrein inhibitor units of aprotinin, and 1.7 mg pancreatic elastase are then added to the pooled protein fractions and the solution is incubated at room temperature with gentle stirring for 5 hours. The reaction is terminated by addition of methoxysuccinyl-(-ala-ala-pro-val) chloromethylketone to $10^{-4}$M, and stirred for a further 30 minutes. The solution is dialysed overnight at 4° C. against a large volume of 0.1M sodium phosphate buffer, pH 8.0, using tubing with molecular weight cutoff at 6500. 300 mg of dialysed plasminogen solution is applied to a 4.8$\times$15 cm, 230 ml lysine-agarose column equilibrated in 0.3M sodium phosphate buffer, pH 8.0, and mini-plasminogen is eluted in 300 ml of the same buffer. Protein-containing fractions are pooled, benzamidine added to a final concentration of 50 mM, and mini-plasminogen precipitated by the addition of solid ammonium sulfate in several portions to a final concentration of 80% saturation.

Assay of Membrane-Bound Enzyme

Once the immobilized enzyme and the enzyme substrate are prepared, the membrane-bound enzyme may be tested for its ability to convert the enzyme substrate to product. Membrane-bound enzyme is assayed by pumping substrate, either small and synthetic, or macromolecular protein substrates (plasminogens), through the membrane; the former measures the amount of active enzyme bound, whereas the latter yields an estimate of the catalytic capacity of the membrane in plasminogen activation. The membrane to be assayed is mounted in a filter holder (for example, Millipore Nos. SXOOO2500 and SXOOO4700 for 25 mm and 47 mm diameter, respectively), which is connected to a peristaltic pump. Temperature control may be achieved by immersing the substrate reservoir and connecting tubing in a temperature regulated bath. The substrate solution is pumped through the membrane, or several membranes assembled in series, e.g., 1 ml aliquots of the effluent are taken. The absorbance change in the effluent compared with the substrate solution gives the concentration of product which, when multiplied by the flow rate, yields the activity in terms of moles per unit time for small substrates; assay of plasmin using Kabi S-2251 is used for estimating the rate of plasminogen activation. Given the value of apparent $K_{cat}$, which is derived from measurements of enzyme activity in free solution, the estimate of active bound enzyme is easily obtained from the observed rate of product formation. In practice, assay of bound enzyme activity should be made under conditions of perfusion in which no more than 10% of small substrate are hydrolysed; flow rates of 10–15 ml/cm$^2$/h give maximum apparent rates of substrate hydrolysis.

Figure 4A:
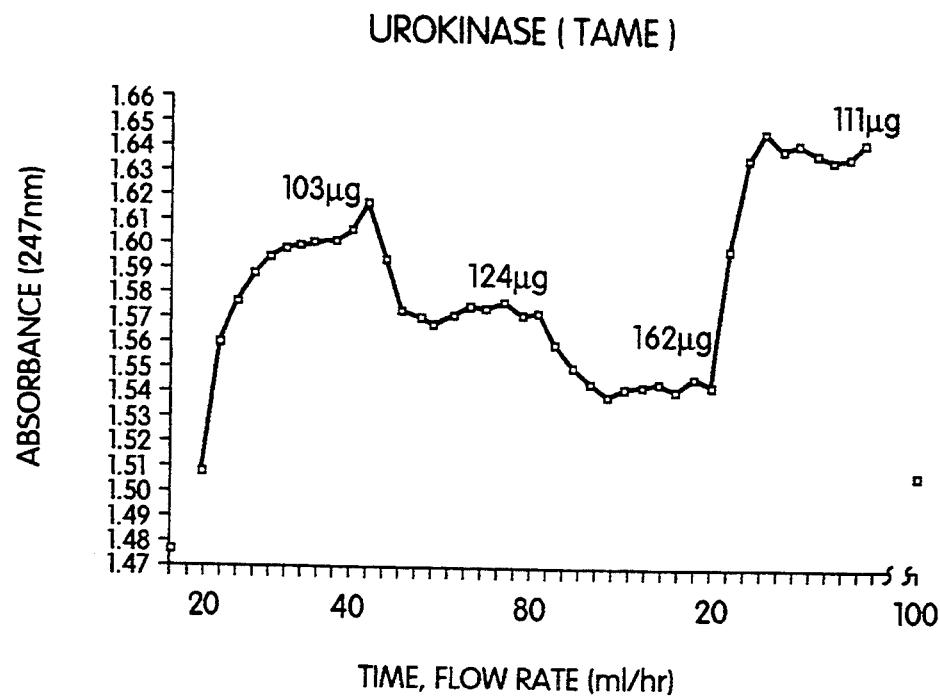
FIGS. 4A and 4B are graphs showing hydrolysis of two different substrates in the presence of membrane-bound enzyme.
Figure 4B:
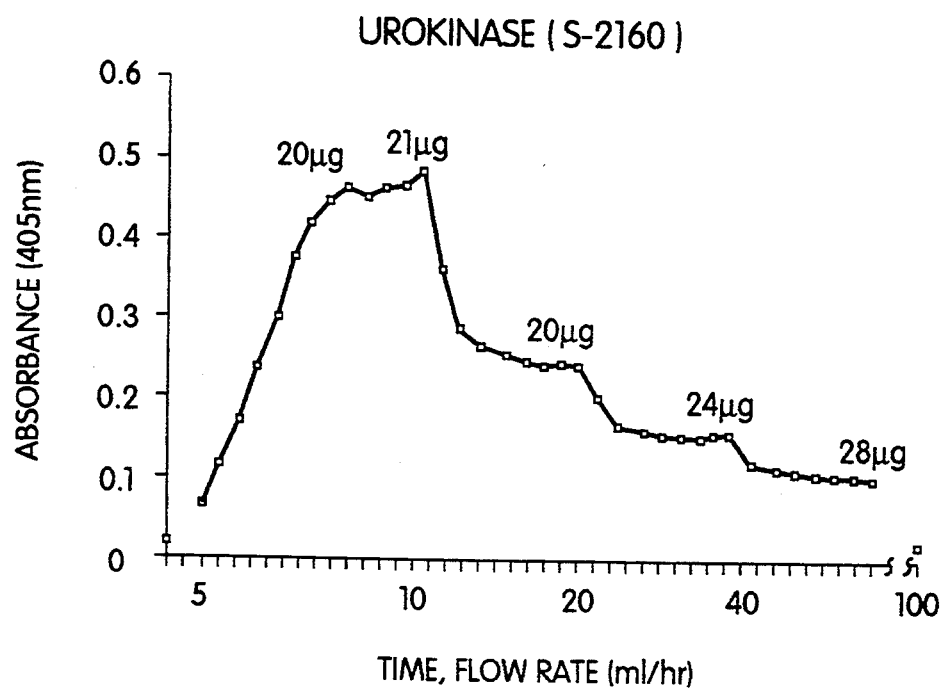

The small substrates dissolved in Tris-HCl buffer (0.1M, pH 8.8) are either TAME (tosyl-L-arginine methylester, 10 mM) or Kabi S-2160 (N-benzoyl-phe-val-arg-p-nitroanilide, 0.2 mM). The hydrolysis of TAME is measured by change in absorbance at 247 nm, and that of Kabi S-2160 at 405 nm. The results of such an assay are shown in FIGS. 4A and 4B. FIG. 4A shows results of an assay of activity of membrane-immobilized urokinase using 10 mm TAME as substrate. Numbers on the horizontal axis denote the initiation of perfusion at the indicated flow rate. Estimates of the total quality of urokinase are indicated for selected points, after equilibration for each flow rate. FIG. 4B shows results of an activity assay of membrane-immobilized urokinase using 0.2 mM Kabi S-2160 as substrate. Flow rates and estimates of active urokinase are as indicated in FIG. 4A.

The macromolecular substrates, glu- and lys-plasminogens as well as truncated forms such as mini- and-/or microplasminogen, are dissolved in 90 mM NaCl, 5 mM NaPO$_4$, pH 7.3–7.5, 1.8% dextrose, usually at a concentration of about 30 μM. Glu-plasminogen is the naturally occurring form of plasmin in circulation; the N-terminal amino acid residue is glutamic acid. Lys-plasminogen is derived from glu-plasminogen by limited proteolysis, usually catalyzed by plasmin, in which a peptide fragment of 77 residues is cleaved from the amino terminal domain, leaving an N-terminal lysine residue. Mini-plasminogen is derived from either glu-or lys-plasminogen by limited proteolysis, catalyzed by pancreatic elastase, in which a fragment containing the proenzyme domain of plasminogen with a single attached kringle, is generated, the remaining 4 kringles and intervening peptides having been separated, as described in Sottrup-Jensen et al. (*Progress in Chem. Fibrinolysis and Thrombosis* 3:191–209, Davison et al., eds., 1978, Raven Press, N.Y.). Micro-plasminogen consists of the proenzyme domain of plasminogen with a stretch of connecting peptide and a few residues of kringle 5 attached at its N-terminus, and is generated by plasmin cleavage of plasminogen (see Shi et al., 1980, *J. Biol. Chem.* 263:17071–17075).

The rate of plasminogen activation, as well as the fraction that is activated to plasmin, are influenced by numerous factors, including plasminogen concentration, flow rate, enzyme-binding area within the reaction zone, and numbers of membranes in series within the reaction zone. These parameters can be adjusted to achieve any desired therapeutic goal in terms of plasmin formed per unit time for any fraction of plasminogen activated. In a typical run, two 47 mm membranes mounted in series will activate approximately 80% of the perfused mini-plasminogen at a concentration of 30 μM and a flow rate of 70 ml/hour, yielding about 1.7 μmoles of plasmin/hour. Membranes can function continuously at constant rates for at least 3 hours.

When membrane coupling is performed, 80% of available urokinase is removed from solution and bound to the membrane. Of this amount, 20–25% is catalytically active in hydrolysis of small substrates, and approximately 5% is active in plasminogen activation.

In order to attain therapeutically useful levels of plasmin, the plasmin-generating injection/activation apparatus should be easily perfusible at low pressures, physically compact, and capable of maintaining a relatively high rate of plasminogen activation, i.e., conversion of at least 75% of the perfused plasminogen, or at least 2 μmoles of plasmin per hour for several hours.

Use of Injection/Activation Apparatus

The injection/activation apparatus may be tested for in vivo use in dissolving blood clots by introducing a radioactive clot into, e.g., the external jugular vein of a dog, and injecting plasmin using the apparatus of the invention into the dog's circulatory system. Dissolution of the clot may be followed by monitoring the level of radioactivity; a decrease in the level of radioactivity at the site of the clot indicates dissolution of the clot.

Dosage

The dosage of drug administered to a patient using the apparatus of the invention will vary depending upon the type of drug to be administered. For example, the duration of fibrinolytic/fibrinogenolytic treatment using the apparatus of the invention may vary from a short single dose administration of plasmin, e.g., in myocardial infarction, to the longer thrombolytic regimens required for thrombophlebitis and pulmonary embolism or the prolonged, continuous and/or intermittent treatments which may be used to treat coronary occlusion and other conditions, such as hyperfibrinogenemia, for which prophylactic therapy may be desirable. A longer thrombolytic or fibrinolytic/fibrinogenolytic therapy will require adjustment depending upon the size of clot or the ultimate desired level of circulating fibrinogen. If a small reduction in fibrinogen concentration is required, more frequent administrations of low doses may be needed to maintain a given depression of the fibrinogen level. Persons at risk for thrombus formation include but are not limited to diabetics and pregnant women. Diabetics carry a higher than normal level of fibrinogen and, therefore, have a higher risk of developing thrombi. The administration of plasmin prophylactically to a diabetic would lower fibrinogen levels and thus reduce the risk of clot formation.

The duration of fibrinolytic and or fibrinogenalytic treatment using the injection/activation apparatus of the invention may vary from a short single dose administration of plasmin, e.g., 1–30 μmoles of plasmin for a 150 lb. person within a 6 hour period, depending upon the size and location of the clot. For example, if the clot is venous, the duration of treatment may be days, whereas if the clot is arterial, only hours of treatment may be required.

Other factors must be taken into account when using the injection/activation apparatus of the invention to administer a drug, e.g., of primary importance is the nature of the drug itself. The following information would be used to assess the administration of the drug plasmin to a human patient using the injection/activation apparatus of the invention.

Clot dissolution reflects the fibrinolytic/fibrinogenolytic action of plasmin, and the duration and effectiveness of thrombolytic therapy following administration of plasmin depend primarily on the balance between the rates of plasmin introduction, and plasmin removal and/or inhibition by the plasmin inhibitor, $\infty$2-antiplasmin, or other inhibitors of plasmin. Factors to be taken into account when adjusting plasmin dosage for clot dissolution include physical factors such as height, weight, and age of the patient; the location of the blood clot, and circulating levels of plasmin inhibitors, such as $\infty$2-antiplasmin and $\infty$2-macroglobuiin. $\infty$2-antiplasmin, which has a normal range of plasma concentration in vivo of approximately 1 μM±20%, is ordinarily the dominant factor regulating plasmin action in the circulation; plasmin combines irreversibly with $\infty$2-antiplasmin to form a 1:1 complex and is thereby inhibited before it can attack clots or other proteins. The level of circulating $\infty$2-antiplasmin is important in assessing plasmin dosage, and $\infty$2-antiplasmin must be titrated to a level at which no more than 15% of the normal circulating concentration is present. A high initial level of $\infty$2-antiplasmin will require a large dose of extracorporeal plasmin to be administered parenterally.

Hormone Treatment

Another therapeutic use of the apparatus of the invention involves use of an immobilized proteolytic enzyme, e.g., for prohormone conversion, the process by which inactive hormone precursors are converted to their active forms. Mammalian polypeptide hormone activation typically is mediated by limited proteolysis catalyzed by proteolytic enzymes.

The inactive precursor of the hormone insulin is much more soluble in physiological buffer media than the active hormone itself, and therefore substantially higher concentrations of proinsulin can be maintained in a reservoir of a given size as compared with active form insulin. Proinsulin can be perfused through a membrane containing immobilized plasmin, which converts proinsulin to insulin by limited proteolysis during the course of injection. This procedure allows insulin to be generated during the act of infusion and to enter the bloodstream without forming potentially harmful polymeric aggregates of low solubility.

Preparation of Immobilized Plasmin

Immobilized plasmin is prepared by first immobilizing its inactive precursor plasminogen, and then using a plasminogen activator to convert the plasminogen to plasmin. Plasminogen, preferably in the form of mini- or microplasminogen, is prepared using human or domestic animal blood plasma or plasma fractions for starting material. The resulting plasminogen is immobilized by coupling either to derivatized nylon membrane, e.g., as described above, or to another matrix, e.g., a bead matrix, using standardized procedures familiar to those skilled in the art. Matrix-bound plasminogen is activated to the corresponding plasmin by exposure to a conveniently available plasminogen activator, and washed free of the activator. The plasmin membrane may be tested for plasmin activity in the manner described for the urokinase membrane, but using the plasmin substrate Kabi S-2160 or tosyl-L-arginine methylester, or proinsulin (Novo Pharmaceuticals, Copenhagen, Denmark; Eli Lilly & Company, Indianapolis, Ind.; or produced by conventional recombinant DNA techniques (Nature 282:525–527 (1979)). For prohormone therapy, the plasmin membrane mounted in a filter holder, or a plasmin-containing bead matrix in a cylindrical cartridge, is attached to a reservoir containing a concentrated solution of proinsulin and a pump capable of perfusing the immobilized plasmin. The flow rate is determined by varying the diameter of the plasmin membrane or the length of the column of plasmin beads in the cartridge, the rate of pumping, and the concentration of the proinsulin substrate solution. The flow rate may be adjusted empirically to achieve the desired rate of conversion of single chain proinsulin to two-chain insulin coincident with the injection of insulin into the patient's body.

Drug Activation by Sequestration of Inhibitor on an Insoluble Matrix: Lauryl Sulfate Ion-stabilized Plasmin Plasmin exhibits, like any proteases, a strong tendency to self-digestion, especially under the conditions of high concentration that are encountered during its preparation, storage and formulation for delivery. It is desirable to prevent autolysis in order to preserve catalytic activity. A preferred way of accomplishing such suppression is by the addition of suitable concentrations of lauryl sulfate ions, in the form of sodium lauryl sulfate, which inhibits plasmin-catalyzed autolysis. Lauryl sulfate can be toxic, and therefore should be substantially removed from the plasmin preparation prior to injection. This is conveniently accomplished by passing the solution of plasmin/lauryl sulfate over a matrix or membrane capable of removing lauryl sulfate, either by hydrophobic adsorption and/or ion exchange. Thus, the plasmin is activated coincident with its injection into the patient's body. Other hydrophobic anions or cations which may have the same effect and are removable are sarcosyl, deoxycholate, and cetyltrimethyl ammonium bromide.

All operations are performed under sterile conditions using sterile, pyrogen-free reagents. Plasmin, or one of its truncated forms (mini- or micro-plasmin) is produced by perfusing the corresponding plasminogen through one or more urokinase membranes, prepared as described above. The flow rate, plasminogen concentration, temperature and number of membranes are selected to activate 80–95% of the perfused plasminogen to plasmin; for example, two 47 mm membranes perfused with approximately 30 μM mini-plasminogen at about 50 ml per hour and at 25° C. The effluent may be collected directly into a chilled vessel containing a solution of sodium lauryl sulfate sufficient to yield a final lauryl sulfate concentration of 0.05-1.0%, e.g., 0.5-10% lauryl sulfate in a volume of $H_2O$ one tenth that of the anticipated final volume of effluent to be produced.

Alternatively, to achieve a greater proportion of plasmin in the final product, the effluent may be led through a refrigeration bath and directly onto a column bed of immobilized plasmin inhibitor (e.g. aprotinin), where it is bound in an inhibited state; the material emerging from this bed contains the remaining, unactivated plasminogen which may be recycled onto the urokinase membrane to achieve substantially complete conversion to plasmin. At the termination of plasminogen activation any residual unactivated plasminogen is removed by washing the column bed with PBS buffer, and the plasmin product recovered by elution with 90 mM NaCl-1 mM HCl, collected into a buffered solution of lauryl sulfate, as indicated above, calculated to neutralize the HCl. The inactive plasmin is concentrated by addition of solid ammonium sulfate to 80% of saturation, the precipitated plasmin collected by centrifugation, and the ammonium sulfate removed by dialysis against large volumes of water containing sodium lauryl sulfate at approximately 0.1% and 90 mM NaCl, and the dialyzed plasmin solution lyophilized. For therapeutic administration, the inactive plasmin is reconstituted by addition of sterile, pyrogen-free water containing 1.8% dextrose, 90 mM NaCl and 0.1% lauryl sulfate, final concentrations. The inactive plasmin solution is then perfused through a matrix capable of retaining lauryl sulfate ions and thus removing them from the plasmin preparation. For example, the inactive plasmin solution may be pumped through a column of Extractigel (Pierce Chemical Co., Rockford, Ill.), an adsorbing matrix, at a rate not exceeding 1 ml per $cm^2$ per minute. The lauryl sulfate ions are thus retained by the matrix and reactivated plasmin is produced.

Alternatively, the lauryl sulfate-stabilized plasmin may be activated by contacting it with a plurality of ion exchange resin particles. The particles may vary in size, e.g., from 10-350 mesh, and the resin may be any conventional material capable of attracting lauryl sulfate ions, e.g., AG11 A8 (Bio-Rad Laboratories, Richmond, Calif.).

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Other embodiments of the invention are within the following claims.

What is claimed is:

1. Apparatus for administration of a drug to a patient in active form, said apparatus comprising:
   means defining a prodrug reaction zone comprising an immobilized biological macromolecule operative to modify chemically a stored prodrug to a physiologically compatible, physiologically active drug form;
   means in communication with said reaction zone for establishing parenteral access to the body of a patient; and
   means for transporting a prodrug through said reaction zone at a rate sufficient to contact said prodrug with said biological macromolecule to convert said prodrug to said active drug form and then into the body of a patient.

2. The apparatus of claim 1 wherein said reaction zone comprises a matrix having said biological macromolecules immobilized thereon.

3. The apparatus of claim 1 wherein said biological macromolecule is an enzyme.

4. The apparatus of claim 2, said matrix comprising a porous membrane.

5. The apparatus of claim 4, said porous membrane comprising nylon.

6. The apparatus of claim 2, said matrix comprising insoluble chromatographic beads.

7. The apparatus of claim 1 wherein said immobilized biological macromolecule comprises soluble biological macromolecules selectively retained within said reaction zone.

8. The apparatus of claim 1, said biological macromolecule comprising a plasminogen activator.

9. The apparatus of claim 8, said plasminogen activator being selected from the group consisting of urokinase and tissue plasminogen activator and analogs thereof.

10. The apparatus of claim 1, said prodrug comprising plasminogen or an analog thereof and said active drug comprising plasmin or a fibrinolytically/fibrinogenolytically active analog thereof.

11. The apparatus of claim 3 wherein said enzyme comprises a protease.

12. The apparatus of claim 1, said prodrug comprising a prohormone and said active drug comprising a hormone.

13. The apparatus of claim 12, said prohormone comprising proinsulin and said hormone comprising insulin.

14. The apparatus to claim 1 wherein said biological macromolecule comprises an immunoglobulin.

15. Apparatus for fibrinolysis/fibrinogenolysis therapy capable of delivering plasmin to the body of a patient at a rate and concentration independent of the patient's vascular plasminogen concentration, said apparatus comprising:
   a reservoir of ion stabilized plasmin;
   ion removing means for removing ions from said stabilized plasmin thereby to convert said stabilized plasmin to physiologically compatible, fibrinolytically/fibrinogenolytically active form; and
   means defining a flow path for establishing
   flow of stabilized plasmin from said reservoir through said ion removing means, and
   a flow of fibrinolytically/fibrinogenolytically active plasmin from said ion removing means parenterally into the body of said patient.

16. The apparatus of claim 15 wherein said ion removing means is an adsorber that removes ionic or amphipathic detergents that inhibit the autolysis of plasmin.

17. The apparatus of claim 15 wherein said ion removing means comprises an ion exchange resin.

18. The apparatus of claim 15 wherein said reservoir contains lauryl sulfate-stabilized plasmin and said ion removing means removes lauryl sulfate ions.

19. Apparatus for fibrinolysis/fibrinogenolysis therapy capable of delivering a fibrinolytically/fibrinogenolytically active protein to a patient's body at a concentration independent of the patient's vascular plasminogen concentration, said apparatus comprising:
   a reservoir of protein-prodrug selected from the group consisting of plasminogen, a serine protease-activatable analog of plasminogen, and a mixture thereof;
   a protein-prodrug reaction zone comprising an immobilized biological macromolecule operative to convert said protein-prodrug to a fibrinolytically/fibrinogenolytically active protein; and
   means defining a flowpath for establishing
      a flow of protein-prodrug from said reservoir to said protein-prodrug reaction zone and
      a flow of fibrinolytically/fibrinogenolytically active protein from said reaction zone parenterally into the body of said patient.

20. The apparatus of claim 19 wherein said reaction zone comprises a matrix having a plasminogen activator bound thereto.

21. The apparatus of claim 19 wherein said means defining a flowpath comprises a conduit communicating between said reaction zone and a trocar for accessing the body of said patient.

22. The apparatus of claim 19 wherein the protein prodrug is selected from the group consisting of mini-plasminogen, micro-plasminogen, lys-plasminogen and glu-plasminogen.

23. Apparatus for delivering to a site of action an autolytic protease in an active form, said apparatus comprising:
   a reservoir of an autolytic enzyme preparation stabilized by the presence of lauryl sulfate ions;
   ion removing means for removing lauryl sulfate ions from said preparation thereby to convert said stabilized preparation to physiologically compatible, enzymatically active form; and
   means defining a flow path for establishing
      a flow of stabilized preparation from said reservoir and through said ion removing means, and
      a flow of physiologically compatible, active enzyme from said ion removing means to the site of action.

24. The apparatus of claim 23 wherein the site of action is the human body, said apparatus further comprising means for parenteral delivery of said active enzyme into the body.

25. The apparatus of claim 23 wherein said ion removing means is an ion adsorber that removes ionic or amphipathic detergents that inhibit the autolysis of plasmin.

26. The apparatus of claim 23 wherein said ion removing means comprises an ion exchange resin.

* * * * *

UNITED STATES PATENT AND TRADEMARK OFFICE
CERTIFICATE OF CORRECTION

PATENT NO. : 5,378,232            Page 1 of 2
DATED : Jan. 3, 1995
INVENTOR(S) : Thomas G. Easton, et al.

It is certified that error appears in the above-indentified patent and that said Letters Patent is hereby corrected as shown below:

Column 8, line 32, "less of activity" should read --loss of activity--.

Column 11, line 29, "∞2-antiplasmin," should read --$\alpha$2-antiplasmin,--.

Column 11, line 34, "∞2-antiplasmin and ∞2-macroglobuiin." should read --$\alpha$2-antiplasmin and $\alpha$2-macroglobulin.--.

Column 11, line 35, "∞2-antiplasmin," should read --$\alpha$2-antiplasmin,--.

Column 11, line 39, "∞2-antiplasmin" should read --$\alpha$2-antiplasmin--.

Column 11, line 41, "∞2-antiplasmin" should read --$\alpha$2-antiplasmin--.

Column 11, lines 42-43, "∞2-antiplasmin" should read --$\alpha$2-antiplasmin--.

Column 11, line 45, "∞2-antiplasmin" should read --$\alpha$2-antiplasmin--.

UNITED STATES PATENT AND TRADEMARK OFFICE
CERTIFICATE OF CORRECTION

PATENT NO. : 5,378,232  Page 2 of 2
DATED : Jan. 3, 1995
INVENTOR(S) : Thomas G. Easton, et al.

It is certified that error appears in the above-indentified patent and that said Letters Patent is hereby corrected as shown below:

Column 14, line 44, "The apparatus to" should read --The apparatus of--.

Signed and Sealed this

Nineteenth Day of September, 1995

Attest:

BRUCE LEHMAN

Attesting Officer      Commissioner of Patents and Trademarks